(12) United States Patent
Lee et al.

(10) Patent No.: US 11,557,401 B2
(45) Date of Patent: Jan. 17, 2023

(54) METHOD AND APPARATUS FOR PREDICTING IMPORTED INFECTIOUS DISEASE INFORMATION BASED ON DEEP NEURAL NETWORKS

(71) Applicant: KOREA ADVANCED INSTITUTE OF SCIENCE AND TECHNOLOGY, Daejeon (KR)

(72) Inventors: Jae-Gil Lee, Daejeon (KR); Minseok Kim, Daejeon (KR); Junhyeok Kang, Daejeon (KR); Doyoung Kim, Daejeon (KR); Hwanjun Song, Daejeon (KR); Hyangsuk Min, Daejeon (KR); Youngeun Nam, Daejeon (KR); Dongmin Park, Daejeon (KR)

(73) Assignee: KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 0 days.

(21) Appl. No.: 17/686,632

(22) Filed: Mar. 4, 2022

(65) Prior Publication Data

US 2022/0293282 A1    Sep. 15, 2022

(30) Foreign Application Priority Data

Mar. 5, 2021  (KR) .......................... 10-2021-0029432

(51) Int. Cl.
*G16H 50/80*          (2018.01)
(52) U.S. Cl.
CPC .................... *G16H 50/80* (2018.01)
(58) Field of Classification Search
CPC ...................................................... G16H 50/80
See application file for complete search history.

(56) References Cited

U.S. PATENT DOCUMENTS

2010/0042394 A1*  2/2010  Khan .................. G16H 50/80
                                                    703/11

FOREIGN PATENT DOCUMENTS

JP    2015-038708    2/2015
KR    10-1244252     3/2013
                (Continued)

OTHER PUBLICATIONS

Adiga, Aniruddha, et al. "Data-driven modeling for different stages of pandemic response." Journal of the Indian Institute of Science 100.4 (2020): 901-915. (Year: 2020).*

(Continued)

*Primary Examiner* — Robert W Morgan
*Assistant Examiner* — Chance L Smith
(74) *Attorney, Agent, or Firm* — Lex IP Meister, PLLC

(57) ABSTRACT

A method for operating an apparatus for predicting confirmed cases of an infectious disease is provided. The method comprises predicting infectious disease information per country, including an infection risk per country, expected number of entrants per country, and number of imported cases per country, based on collected epidemic statistics data per country and inflow data between a corresponding country and a destination country, grouping two or more countries based on geographic or economic relevance, and correcting the infectious disease information per country of countries within a grouped group according to a contagion risk impact set depending on a correlation between the countries within the group, and predicting total number of imported cases flowing into the destination country by re-correcting the infectious disease information per country through applying a correlation for the confirmed cases of the infectious disease between groups to the infectious disease information per country.

5 Claims, 11 Drawing Sheets

(56) References Cited

FOREIGN PATENT DOCUMENTS

| KR | 10-1911466 | 10/2018 | | |
|---|---|---|---|---|
| KR | 10-1960504 | 7/2019 | | |
| KR | 10-2140096 | 7/2020 | | |
| KR | 102140096 B1 | * 7/2020 | ............. | G16H 50/80 |
| WO | WO-2013120199 A1 | * 8/2013 | ......... | G06F 16/2228 |

OTHER PUBLICATIONS

Arun, Shreyas Setlur, and Ganesh Neelakanta Iyer. "On the analysis of COVID19-novel corona viral disease pandemic spread data using machine learning techniques." 2020 4th International Conference on Intelligent Computing and Control Systems (ICICCS). IEEE, 2020. (Year: 2020).*

Bouhamed, Heni. "Covid-19 cases and recovery previsions with deep learning nested sequence prediction models with long short-term memory (LSTM) architecture." Int. J. Sci. Res. in Computer Science and Engineering 8.2 (2020). (Year: 2020).*

Ding, Xiaoye, et al. "Incorporating dynamic flight network in SEIR to model mobility between populations." Applied Network Science 6.1 (2021): 1-24. (Year: 2021).*

Ibrahim, Mohamed R., et al. "Variational-LSTM autoencoder to forecast the spread of coronavirus across the globe." PloS one 16.1 (2021): e0246120. (Year: 2021).*

Lesmanawati, Dyah AS, et al. "A rapid risk analysis tool to prioritise response to infectious disease outbreaks." BMJ Global Health 5.6 (2020): e002327. (Year: 2020).*

Liu, Fenglin, et al. "Predicting and analyzing the COVID-19 epidemic in China: Based on SEIRD, LSTM and GWR models." PloS one 15.8 (2020): e0238280. (Year: 2020).*

Shahid, Farah, Aneela Zameer, and Muhammad Muneeb. "Predictions for COVID-19 with deep learning models of LSTM, GRU and Bi-LSTM." Chaos, Solitons & Fractals 140 (2020): 110212. (Year: 2020).*

Salami, Donald, et al. "Dengue importation into Europe: a network connectivity-based approach." PLoS One 15.3 (2020): e0230274. (Year: 2020).*

Yang, Zifeng, et al. "Modified SEIR and AI prediction of the epidemics trend of COVID-19 in China under public health interventions." Journal of thoracic disease 12.3 (2020): 165. (Year: 2020).*

Tatem, Andrew J., et al. "The geography of imported malaria to non-endemic countries: a meta-analysis of nationally reported statistics." The Lancet Infectious Diseases 17.1 (2017): 98-107. (Year: 2017).*

Minseok Kim et al., "Hi-COVIDNet: Deep Learning Approach to Predict Inbound COVID-19 Patients and Case Study in South Korea", KDD '20: Proceedings of the 26th ACM SIGKDD International Conference on Knowledge Discovery & Data Mining, pp. 3466-3473, Aug. 2020.

Yuexin Wu et al., "Deep learning for epidemiological predictions", In Proceedings of 41st International ACM SIGIR Conference on Research and Development in Information Retrieval (2018), pp. 1085-1088.

Vinay Kumar Reddy Chimmula et al. "Time series forecasting of COVID-19 transmission in Canada using LSTM networks", Chaos, Solitons & Fractals (2020), 109864.

* cited by examiner

METHOD AND APPARATUS FOR PREDICTING IMPORTED INFECTIOUS DISEASE INFORMATION BASED ON DEEP NEURAL NETWORKS

CROSS-REFERENCE TO RELATED APPLICATION

This application claims priority to and the benefit of Korean Patent Application No. 10-2021-0029432 filed in the Korean Intellectual Property Office on Mar. 5, 2021, the entire contents of which are incorporated herein by reference.

BACKGROUND

(a) Field

The present disclosure relates to the technology of predicting imported infectious diseases.

(b) Description of the Related Art

Infection and spread caused by the appearance of new pathogens are continuing, as various factors, such as adaptation and mutation of pathogens, the ecological change caused by industrial development, the climate change, increase in personal exchanges and material exchanges, and economic plight, are changing. In particular, since types of foreign infectious diseases to be feared to flow into a country are diversified and information, knowledge, and experience on the infectious diseases are insufficient, there are difficulties in diagnosing and responding to the infectious diseases.

World Health Organization (WHO) declared the COVID-19 outbreak a "pandemic". The threat of the COVID-19 pandemic continues to increase worldwide through physical contact between people, thereby putting people in great danger. Owing to the high contagion rate of the disease, inbound infected patients might lead to a destructive pandemic, eventually paralyzing an entire country. To address this, most governments impose quarantines to monitor overseas inflow and prevent this infectious disease from entering across countries. Typically, epidemics come from abroad. The objective must be to allow a flow of uninfected travelers to avoid stopping economic activity.

Regarding the control of overseas entrants, all symptomatic entrants from abroad go through diagnostic tests at the airport. Those who test positive are transferred to a hospital or a community treatment center. The asymptomatic passengers (those who did not show symptoms of the disease) receive diagnostic tests at the airport if they come from Europe, and short-term foreigners are quarantined at government facilities. To operate this special entry procedure, the government must allocate resources, such as medical staff, diagnostic kits, and quarantine facilities, in advance, and then adjust the procedure to a potential new situation rapidly. Thus, it is very useful to precisely predict the number and trend of imported cases accurately.

For this, studies for predicting a future trend of infectious diseases from a trend of confirmed cases from a certain time point in the past to the present are being conducted. However, in most of such studies, epidemic statistics data are merely used but the various external factors affecting the trend of infectious diseases are not considered. In particular, the trend of confirmed cases flowing into a country from abroad is affected by various factors throughout the world, which makes it difficult to predict the trend.

SUMMARY

The present disclosure provides the method and the apparatus that predict imported infectious disease information based on deep neural network.

The present disclosure provides the method and the apparatus that predict the number of imported cases for the near future, using a hierarchical prediction model with a country-level encoder and a group (e.g., continent)-level encoder.

The present disclosure provides a prediction model. The prediction model predicts infectious disease information, including an infection risk per country and a degree of exchange with a destination country, based on epidemic statistics data per country, corrects infectious disease information per country by using a contagion risk impact between countries having geographical or economical relevance, and then predicts information on confirmed cases of an infectious disease.

According to an embodiment, a method for operating an apparatus for predicting confirmed cases of an infectious disease is provided. The method includes predicting infectious disease information per country, including an infection risk per country, expected number of entrants per country, and number of imported cases per country, based on collected epidemic statistics data per country and inflow data between a corresponding country and a destination country; grouping two or more countries based on geographic or economic relevance, and correcting the infectious disease information of countries within each group according to a contagion risk impact set depending on a correlation between the countries within the group; and re-correcting the infectious disease information per country, by applying a correlation for the confirmed cases between groups to the infectious disease information per country, and predicting total number of imported cases flowing into the destination country.

The epidemic statistics data per country may include one or more of number of daily confirmed cases, number of deaths, an infection derivative index, search keywords data related to infectious disease. The inflow data may include one or more of number of customers having subscribed to a roaming service per country, arrival and departure status data per country, number of airlines entering into a country, and flight records of the airlines.

The predicting the infectious disease information per country may include deriving the infection risk per country and a trend of infectious disease at a current time based on the epidemic statistics data per country, and estimating a degree of exchange per country with the destination country based on the inflow data, and predicting the expected number of entrants per country and the expected number of imported cases per country based on the infection risk, the trend of infectious disease, and the degree of exchange.

The predicting the infectious disease information per country may include classifying the epidemic statistics data per country and the inflow data by country and preprocessing the classified data into an input format of a trained risk prediction model per country, and inputting preprocessed data into the risk prediction model per country, and deriving the infection risk per country, the trend of infectious disease per country, and the infectious disease information per country by highlighting a period with a singularity on a spread of the infectious disease in each country.

The correcting the infectious disease information per country may include inputting the infection risk per country, the trend of infectious disease per country, and the predicted infectious disease information per country into a trained risk prediction model per country, and correcting the infectious disease information per country according to the contagion risk impact of countries within each group. The contagion risk impact may be automatically derived during learning of the risk prediction model per group.

The predicting the total number of imported cases may include, inputting the corrected infectious disease information per country into a trained converged risk prediction model, re-correcting the infectious disease information per country by group unit according to the correlation for the confirmed cases between groups, and using the re-corrected infectious disease information per country, predicting the number of imported cases per country, number of imported cases per group, and the total number of imported cases. The correlation for the confirmed cases between groups may be automatically derived during learning of the converged risk prediction model.

The method may further include processing one or more data or information of the total number of imported cases, the infection risk per country, a trend of infectious disease per country, the corrected infectious disease information per country, and the re-corrected infectious disease information per country, as visualized data, and providing the visualized data.

According to another embodiment, a method for operating an apparatus for predicting confirmed cases of an infectious disease is provided. The method includes generating training data by matching input data for an arbitrary period with result data corresponding to a prediction period following the arbitrary period, from collected epidemic statistics data per country; and inflow data between a corresponding country and a destination country, and training one or more risk prediction models to derive matched result data from the input data at each training cycle. The training the risk prediction model includes hierarchically training under a process to: predicting number of imported cases based on expected number of entrants per country through respectively deriving an infection risk per country, a trend of infectious disease, a degree of exchange from the input data; grouping two or more countries based on geographic or economic relevance; correcting the number of imported cases based on correlation for confirmed cases of the infectious disease between groups and a contagion risk impact set according to a correlation between grouped countries; and outputting the corrected number of imported cases, as the result data.

The risk prediction model may include a risk prediction model of each country that predicts infectious disease information, including the number of confirmed cases flowing into each country, based on the infection risk by country unit and a degree of exchange between a corresponding country and a destination country, a risk prediction model of each group that corrects the number of imported cases per country according to the contagion risk impact of countries grouped based on geographic or economic relevance, and a converged risk prediction model that predicts total number of imported cases to the destination country by re-correcting the infectious disease information per country, by applying a correlation for confirmed cases between groups to the corrected infectious disease information per country by group unit.

The risk prediction model of each country may derive the infection risk and the trend of infectious disease at a current time by highlighting a period with a singularity on a spread of the infectious disease in epidemic statistics data per country. The epidemic statistics data per country may include one or more of number of daily confirmed cases, number of deaths, an infection derivative index, and search keywords data related to infectious diseases. The risk prediction model per country may estimate degree of exchange with the destination country per country based on inflow data. The inflow data may include one or more of number of customers having subscribed to a roaming service per country, arrival and departure status data per country, number of airlines entering into a country, and flight records of the airlines. The risk prediction model per country may predict expected number of entrants per country and the number of imported cases per country, based on the infection risk, the trend of infectious disease, and the degree of exchange.

The contagion risk impact may be automatically derived according to a correlation between countries based on the infection risk and the trend of infectious disease of countries within each group, during learning process of the risk prediction model per group. The correlation for confirmed cases between groups may be automatically derived based on the infection risk by group unit and the trend of infectious disease of group unit, during learning of the converged risk prediction model.

The training the risk prediction model may include calculating a hierarchical loss based on a result of number of imported cases predicted or corrected by each model, after successively training the risk prediction model per country, the risk prediction model per group, and the converged risk prediction model, and updating parameters of the risk prediction model per country, the risk prediction model per group, and the converged risk prediction model, based on a loss of each layer, through error backpropagation so that the calculated hierarchical loss is minimized.

According to still another embodiment, a computing device is provided. The computing device includes a memory including instructions, and at least one processor that predicts number of imported cases into a destination country based on input epidemic statistics data per country and inflow data between a corresponding country and a destination country, by executing the instructions. The processor predicts infectious disease information per country, including an infection risk per country, expected number of entrants per country, and number of imported cases per country, by inputting collected epidemic statistics data per country and inflow data between a corresponding country and a destination country into a trained risk prediction model per country, and provides number of confirmed cases to flowing into the destination country, by grouping two or more countries based on geographic or economic relevance, inputting the infection risk per country and the infectious disease information of countries within each group into a trained risk prediction model per group, and correcting the infectious disease information per country based on a contagion risk impact set according to a correlation between countries within a group.

The trained risk prediction model per country may derive the infection risk and a trend of infectious disease at a current time, by highlighting a period with a singularity on a spread of the infectious disease in epidemic statistics data per country. The epidemic statistics data per country may include one or more of number of daily confirmed cases, number of deaths, an infection derivative index, and search keywords data related to infectious diseases. The trained risk prediction model per country may estimate a degree of exchange per country with the destination country based on inflow data. The inflow data may include one or more of number of customers having subscribed to a roaming service per country, arrival and departure status data per country, number of airlines entering into a country, and flight records of the airlines. The trained risk prediction model per country may predict expected number of entrants per country and the expected number of imported cases per country, based on the infection risk, the trend of infectious disease, and the degree of exchange.

The contagion risk impact may be a weight that is set for the risk prediction model per group according to a correlation between countries based on the infection risk and the trend of infectious disease of countries within each group, during learning process of the risk prediction model per group.

The processor may input the corrected infectious disease information per country into a trained converged risk prediction model, acquire the infectious disease information per country re-corrected by group unit based on the correlation for confirmed cases between groups, and predict total number of confirmed cases flowing into the destination country.

The processor may process, one or more data or information of the total number of imported cases, the infection risk per country, the trend of infectious disease per country, the corrected infectious disease information per country, and the re-corrected infectious disease information per country, as visualized data, and provides the visualized data.

As described above, according to an embodiment, confirmed cases flowing from abroad can be precisely estimated by considering external factors, such as a degree of exchange between a corresponding country and a destination country and a contagion risk impact between neighboring countries, in addition to epidemic statistics data. Further, domestic spread may be prevented through preemptive reinforcement of immigration inspection based on the predicted number of imported cases.

According to the present disclosure, by predicting the number of confirmed cases from abroad, a quarantine policy can be established and resources can be allocated in advance. As a result, national risk caused by infectious diseases flowing from abroad can be minimized.

DETAILED DESCRIPTION OF THE EMBODIMENTS

Figure 1:
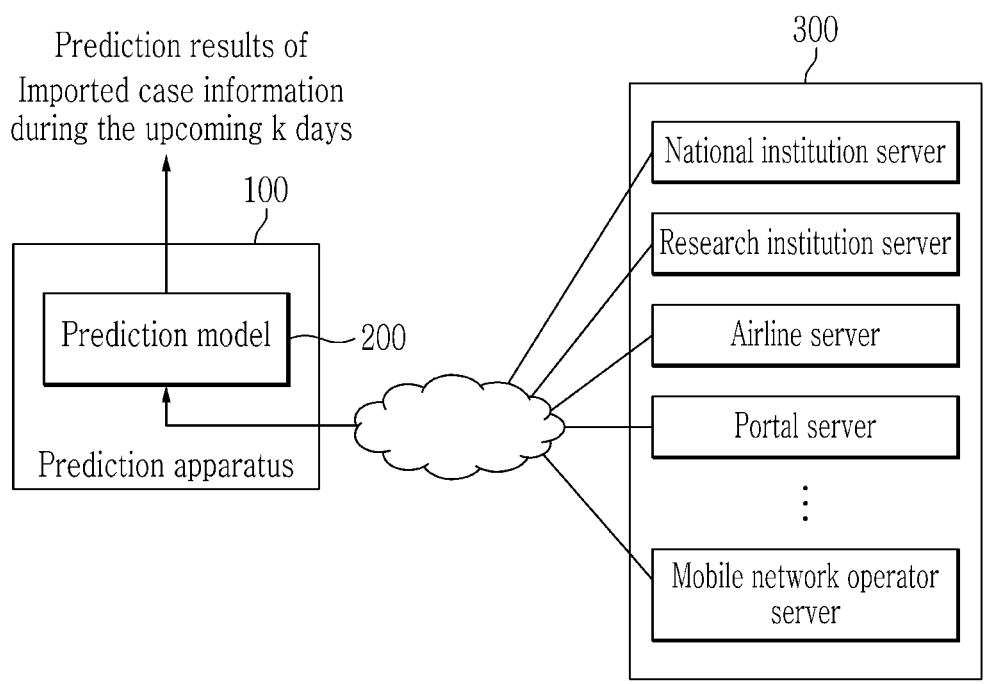
FIG. 1 is a diagram illustrating an apparatus for predicting information on imported cases of an infectious disease and servers connecting with the apparatus according to an embodiment.

Hereinafter, embodiments of the present disclosure will be described in detail with reference to the attached drawings so that the person of ordinary skill in the art may easily implement the present disclosure. However, the present disclosure may be modified in various ways and is not limited to the embodiments described herein. In the drawings, elements irrelevant to the description of the present disclosure are omitted for simplicity of explanation, and like reference numerals designate like elements throughout the specification.

In the description, when a part is referred to "include" a certain element, it means that it may further include other elements rather than exclude other elements, unless specifically indicates otherwise.

The devices described in the present disclosure comprises a hardware including at least one processor, a memory, a communication device, and the like, and a computer program executed in combination with the hardware is stored in a predetermined space. The hardware may have configuration and performance available for implementing a method of the present disclosure. The computer program includes instructions implementing the operation method of the present disclosure described with reference to the accompanying drawings and performs the present disclosure in combination with hardware such as a processor and a memory.

In the description, the terms "transmit or provide" may be used to include not only direct transmission or provision but also indirect transmission or provision through another device or by using a bypass.

Throughout the specification, the singular forms "a", "an", and "the" are intended to include the plural forms as well, unless the explicit expression such as "one" or "singular" is used.

In the description, throughout the drawings, the same reference numeral refers to the same element, and "and/or" includes all combinations of each and at least one of the mentioned elements.

In the description, terms including ordinal numbers such as "first", "second", and the like may be used to describe various elements, but the elements are not limited by the terms. The terms are used only to discriminate one element from another. For example, a first element may be referred to as a second element, or similarly, the second element may be referred to as the first element, without departing from the scope of the present disclosure.

In the description, the operation order described in the flowchart may be changed, several operations may be merged, certain operations may be divided, and specific operations may not be performed.

In the description, data and dataset may be used interchangeably.

In the description, a confirmed case of an infectious disease that flows into a destination country from another country is briefly referred to as an imported case. In the description, COVID-19 may be described as an example of the infectious disease. In the description, Korea may be described as an example of the destination country.

FIG. 1 is a diagram illustrating an apparatus for predicting information on imported cases of an infectious disease and servers connecting with the apparatus according to an embodiment.

Referring to FIG. 1, an apparatus 100 (briefly, referred to as a predictor) for predicting confirmed cases of an infectious disease operated by at least one processor outputs, as a prediction result, information on imported cases that flows into a destination country for next k days. The predictor 100 may be provided the prediction result through a prediction model 200 trained to predict the imported case information from input data.

The imported case information may be provided in various ways according to training of the prediction model 200 or processing method of the prediction result. For example, the imported case information may be number of imported cases to the destination country for the next k days or an inflow risk expected in the destination country for the next k days. For example, the predictor 100 can predict number of entrants and imported cases to the destination country from each country through the prediction model 200, and may output the inflow risk, being a ratio of the imported cases to the entrants, as the prediction result. Hereinafter, it is described that a final prediction result is mainly the number of imported cases. The predictor 100 is loaded with a computer program for an operation described in the present disclosure, and the computer program is executed by a processor.

The predictor 100 collects information related to various infectious diseases to be used as an input of the prediction model 200. The predictor 100 may collect various information related to infectious diseases to be used for training the prediction model 200. The predictor 100 may collect various infectious disease-related data from various domestic and foreign external servers 300 such as a national institution server, a research institution server, a transportation server (an airline server, etc.), an Internet portal server, a mobile network operator server, and the like. Here, the infectious disease-related data may be public data or private data for which information provision is agreed with a corresponding institution. For example, the predictor 100 may access a public data portal which provides an open application program interface (API) and collect epidemic statistics data throughout the world (e.g., the number of confirmed cases, the number of deaths, and the like). For convenience of explanation, the predictor 100 is shown to collect data directly from an external server 300 via a network, but infectious disease-related data may be collected from a separate data providing device.

In addition, the prediction model 200 may be trained by a separate training device. However, for convenience of explanation, it is assumed that the predictor 100 trains the prediction model 200 and training data is generated based on the infectious disease-related data collected from the external server 300.

The prediction model 200 is an artificial intelligence model that learns at least one task, and may be composed of, for example, deep neural networks. The prediction model 200 may be implemented as a computer program executed on a computing device. A computer program is stored in a storage medium (non-transitory storage media), and includes instructions described for a processor to execute an operation of the present disclosure. The computer program may be downloaded via a network or sold as a product.

The prediction model 200 may be configured as a hierarchical prediction model that hierarchically predicts the information on imported cases into the destination country for next k days. The prediction model 200 can predict infectious disease information per country, can predict infectious disease information by group including grouped countries, and can finally predict the information on imported cases from the infectious disease information predicted in a previous layer. The prediction model 200 may learn a hierarchical loss in a network structure where a prediction per country, a prediction per group, and a final prediction are hierarchically separated. The prediction model 200 may learn a correlation between countries within a group and a correlation between groups for the destination country through a hierarchical learning process. The infectious disease information per country predicted in a lowest layer may be corrected by a contagion risk impact set according to the correlation between countries within a group and the correlation between groups for the destination country, while sequentially passing through the following layers.

For example, the prediction model 200 may be composed of a risk prediction model of each country (country level encoder), a risk prediction model of each group (group level encoder), and a converged (integrated or unified) risk prediction model. The risk prediction model of each country can extract infectious disease information per country which indicates an impact on the destination country caused by each country. The risk prediction model of each group can extract the infectious disease information per group to which countries belong, from the infectious disease information per country. The converged risk prediction model can extract the information on imported cases (e.g., the total number of imported cases) from the infectious disease information per group. The risk prediction model of each country may be allocated to each country of which the infectious disease-related information can be collected, and the risk prediction model of each group may be configured to be a smaller number than that of the risk prediction model or each country. Here, the group may be configured in consideration of geographic/economic relevance between countries, and at least one country is included in each group. The group may be simply classified into continents to which the countries belong. Alternatively, the predictor 100 may receive data on geographic location and economic cooperation relationship between countries, and may classify geographical/economically related countries into a group based on the received data.

The potential number of imported cases from a country may be represented as a function of inbound passengers arriving from that country and its respective degree of infection risk. The number of imported cases from a country is proportional to the number of inbound passengers arriving from that country and the number of confirmed cases. However, the underlying relationship inside the function is too complex for simplification given that various factors change over time. For instance, a rapid spread of the disease within a country increases the pandemic risk of other countries immediately, while it also decreases inter-country interactions that are proportional to the infection risk. Simultaneously, a country tends to interact with nearby countries in the same continent more often than distant ones in other continents.

As such, in order to accurately predict the number of imported cases, various external factors affecting a trend of an infectious disease should be considered, which causes high complexity in the prediction. Thus, predicting the number of imported cases usually ends up considering only one-to-one relationship between countries.

Unlike the prior art, the prediction model 200 can predict the information on imported cases by reflecting a complex spatio-temporal relationship that affects a spread of the infectious disease, through the hierarchical network model. That is, from the epidemic statistics data during a certain period, the prediction model 200 can extract the infection risk, the trend of infectious disease, and the like over time, and can further extract a degree of exchange from each country to the destination country based on inflow data of each country with the destination country. The prediction model 200 can classify countries into geographically/economically related groups, and extract the infectious disease information per group through correcting and integrating the infectious disease information per country including the infection risk, the trend of infectious disease, and the degree of exchange within each group. The prediction model 200 can predict the information on imported cases by correcting and integrating the infectious disease information per group on group basis. In this case, in the prediction model 200, a correlation between geographically/economically related countries within a group and a correlation between groups for the destination country are set as network weights through a hierarchical learning process. Therefore, the infectious disease information per country gets to include a contagion risk impact from neighboring countries within a group and the complex spatio-temporal relationship successively corrected based on the correlation between groups, which enables the prediction model 200 to make a precise prediction of the information on imported cases.

The predictor 100 may collect time-series infectious disease-related data defined as in Table 1. The infectious disease-related data may be classified into intra-country data and inter-country data. The intra-country data may include epidemic statistics data of a specific country representing the trend of infectious disease over time. The inter-country data may include inflow data (inbound data) representing an arrival trend into a destination country from the specific country.

The epidemic statistics data may include data related to confirmed cases, such as the number of confirmed cases and the number of deaths collected each day in each country. The epidemic statistics data may further include infectious disease-related search keywords data. A degree of anxiety over an infectious disease may be inferred from a frequency of search keywords in a specific country. The inflow data may include international roaming data including the number of customers who have subscribed to a roaming service, arrival and departure status data per country, and traffic data between countries (the number of airlines entering the country, flight records of an airline, etc.). The traffic data may vary according to transportation means entering into the destination country from another country, and may be air data, ship data, train data, and the like.

TABLE 1

| Dataset | | Variable description |
|---|---|---|
| Intra-Country Data | Confirmed Cases | (1) Date |
| | | (2) Country |
| | | (3) number of confirmed cases |
| | | (4) First derivative of (3) |
| | | (5) Second derivative of (3) |
| | | (6) number of deaths |
| | | (7) First derivative of (6) |
| | | (8) Second derivative of (6) |
| | Search Keywords | (1) Date |
| | | (2) Country |
| | | (3)-(6) number of searches for Disease related keywords such as "COVID-19," "COVID test," "Flu," and "Mask" |
| Inter-Country Data | International Roaming | (1) Date |
| | | (2) Originating country |
| | | (3) Total number of customers arriving in Korea |

TABLE 1-continued

| Dataset | | Variable description |
|---|---|---|
| | Flights | (1) Date |
| | | (2) Originating country |
| | | (3) Total number of airlines arriving in Korea |

Table 1 is an example of the infectious disease-related data including the epidemic statistics data and the inflow data, and may further include various data.

The dataset of confirmed cases represents the number of daily confirmed cases and deaths per country. Additionally, the dataset of Confirmed cases may include their first and second derivatives to obtain the degree of infection speed per country.

The dataset of search keywords may be collected from Google Search Trend for the four keywords in Table 1, which represent the degree of the anxiety on the disease in each country.

The international roaming data is data on people who have subscribed to overseas roaming in the destination country and are scheduled to enter the destination country after leaving the country. The international roaming data may include all information on countries detected while using the international roaming service. For example, when a subscriber of a mobile network operator uses a roaming service while moving several countries, all countries visited by the subscriber may be included. The dataset of international roaming may be collected from Mobile Network Operators of destination country, such as Korea Telecom. The dataset of International Roaming may contain its Korean customers returning to and from South Korea (destination country). The prediction apparatus 100 may extract the number of roaming entrants from each country per day to estimate the total daily inflow.

The dataset of flights may be collected from the airline information system. The dataset of flights may contain the number of daily cargo and passenger airlines arriving at destination country's airports. The dataset of flights may be used as a rough estimate of the number of the entrants from abroad. Given that the roaming dataset covers only travelers, the flight dataset may be used together with the roaming dataset to cover all inbound travelers.

As shown in Table 2, the predictor 100 may collect data of actual imported cases entering the destination country (e.g., Korea) from a group (e.g., continent) to which the countries belong. The dataset of imported cases may contain the daily number of imported cases to the South Korea (destination country). The dataset of imported cases may be categorized by the originating continent corresponding to the group. The daily number of imported cases may be used as the label attribute for training and testing dataset.

TABLE 2

| Dataset | Variable description |
|---|---|
| Imported Cases | (1) Date |
| | (2) Originating continent |
| | (3) Total number of imported cases in Korea |

The predictor 100 may generate training data using the infectious disease-related data described in Table 1 and Table 2, and perform training of the prediction model 200 for a task using the training data. The task can be set variously, and may be, for example, a task for receiving time-series infectious disease-related data per country during before w days from a current time t, and predicting the number of imported cases to the destination country for the next k days from the current time t. For example, the prediction model 200 is a hierarchical prediction model. The prediction model 200 may be trained to extract the infectious disease information per country from the time-series infectious disease-related data per country, to extract the infectious disease information per group through correcting and integrating the infectious disease information of countries within a group, and to predict the total number of imported cases from the infectious disease information per group. Here, the infectious disease information per group may be the number of imported cases per group. A ground truth for the number of imported cases per each group and the total number of imported cases can be labeled by data of actual imported cases shown in Table 2.

The prediction model 200 trained as above-described may receive time-series infectious disease-related data of country unit, successively deliver hierarchical prediction results, and finally output the information on confirmed cases flowing into the destination country for an upcoming certain period. The risk prediction model per group (group level encoder) of the prediction model 200 learns a contagion impact risk between countries within a group while learning a relationship between the infectious disease information per country and the infectious disease information of a group to which the countries belong. Thus, the infectious disease information per country may be corrected by multiplying the input infectious disease information per country and the contagion risk impact between countries. In addition, the converged risk prediction model of the prediction model 200 learns the correlation between groups for the destination country while learning the relationship between the infectious disease information per group and the information on the confirmed cases flowing into the destination country. As a result, the infectious disease information per group (that is, infectious disease information per country included therein) may be corrected by group unit through applying the correlation between groups to the input infectious disease information per group.

If infectious disease information per country is used for predicting the number of imported cases as it is, inaccurate prediction results may be output due to not reflecting the complex spatio-temporal relationship related to infectious diseases. In contrast, through the prediction model 200, the infectious disease information per country is corrected based on the contagion risk impact between countries within the group and re-corrected based on the correlation between groups, thereby reflecting the spatio-temporal relationship related to the infectious disease. Accordingly, the prediction model 200 can more accurately predict the number of imported cases.

Figure 2:
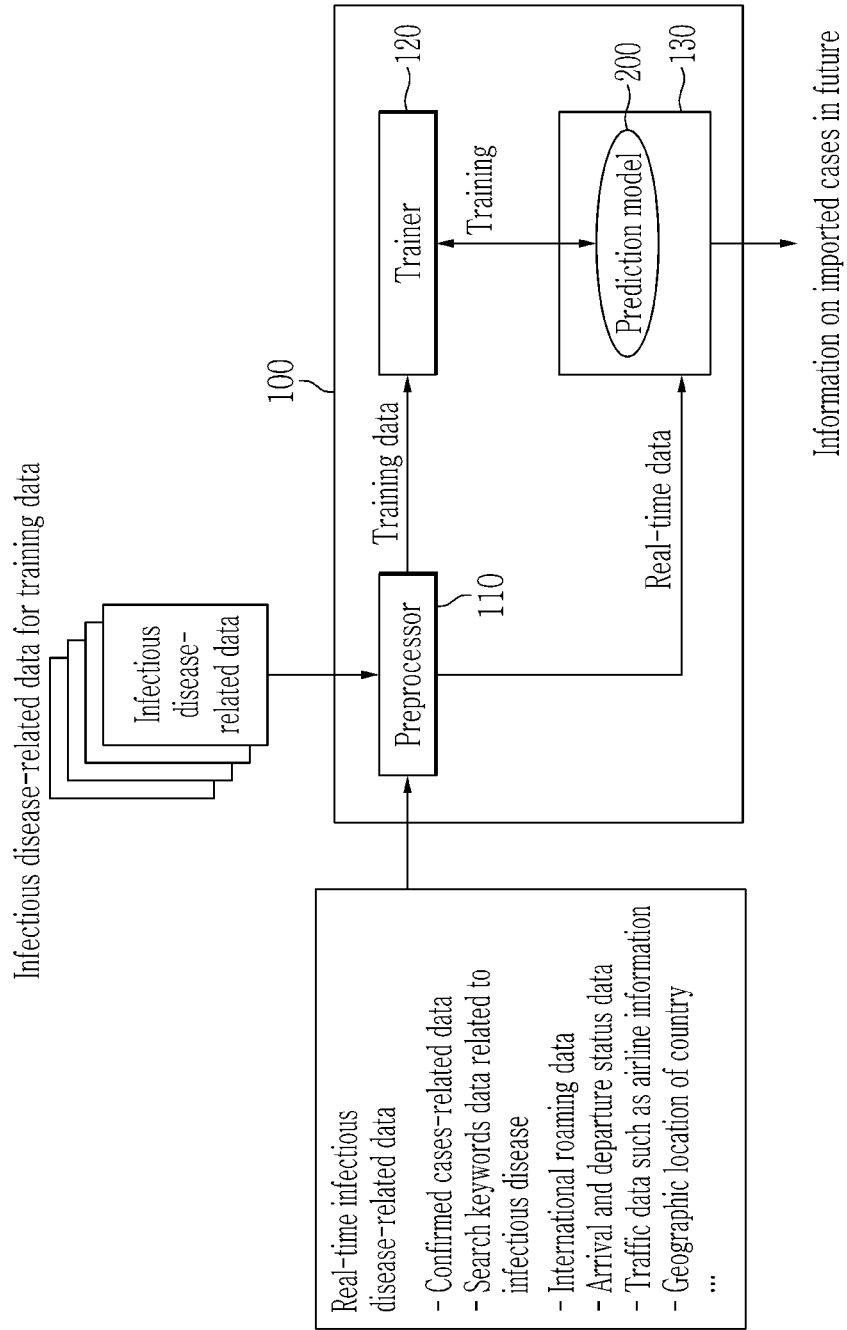
FIG. 2 is a configuration diagram of a prediction apparatus according to an embodiment.

FIG. 2 is a configuration diagram of a prediction apparatus according to an embodiment.

As shown in FIG. 2, a prediction apparatus 100 may include a preprocessor 110, a trainer 120 for training a prediction model 200, and predictor 130 that predicts information on confirmed cases flowing into a destination country using the prediction model 200.

For explanation, the preprocessor 110, the trainer 120, and the predictor 130 are separately named, but they may be operated by at least one processor. Here, the preprocessor 110, the trainer 120, and the predictor 130 may be implemented in a distributed manner on separate computing devices. In this case, they may communicate with each other via a communication interface. For example, since the prediction model having been trained in the trainer 120 may be implemented to interwork with a predictor 130 separately, the trainer 120 and the predictor 130 may be implemented with separate devices. At this time, the computing device may be any device capable of executing a software program written to perform the present disclosure, and may be, for example, a server, a laptop computer, and the like.

The preprocessor 110 receives infectious disease-related data including epidemic statistics data and inflow data collected in real time. The epidemic statistics data may include data related to confirmed cases, such as the number of confirmed cases per country and the number of deaths, search keywords data related to infectious disease per country. The inflow data may include international roaming data, arrival and departure status data, and traffic data such as airline information. In addition, information for classifying countries into groups, such as geographic location of each country and economic cooperation relationship of each country, may be input.

The preprocessor 110 may generate the infectious disease-related data collected up to the current time as real-time input data of the prediction model 200. The real-time input data are classified by country and provided to the prediction model 200.

The preprocessor 110 may generate training data of the prediction model 200 by matching input data with result data among the infectious disease-related data collected during a certain period. The preprocessor 110 generates the training data by matching input data for an arbitrary period with result data corresponding to a prediction period following the arbitrary period. Specifically, the preprocessor 110 may collect the infectious disease-related data including epidemic statistics data, inflow data, and data of actual confirmed cases flowing into a destination country, in order to generate the training data. In order to label a ground truth of the training data, the data of actual confirmed cases flowing into the destination country (e.g., Korea) from a group (e.g., continent) to which the countries belong may be used. The preprocessor 110 may generate the training data by mapping the infectious disease-related data per country during a certain period before the reference time point with the number of actual imported cases during a certain period after the reference time point.

For example, when the infectious disease-related data of about 20 weeks are collected, the preprocessor 110 may set the collected infectious disease-related data of a 1st week to a 18th week as the input data, and may set the number of actual imported cases extracted from the infectious disease-related data of a 19th week to a 20th week as the result data. In addition, the preprocessor 110 may set the collected infectious disease-related data of the 1st week to 10th week as the input data and may generate the training data by using the infectious disease-related data of consecutive 11th week to 12th week as the output data. As described above, the preprocessor 110 may generate the training data by adjusting the arbitrary period in the collected infectious disease-related data.

The trainer 120 trains the prediction model 200 for at least one task based on the training data. The trainer 120 may repeatedly train the prediction model 200 so that the result data (imported case information) is calculated through the input data (epidemic statistics data per country and inflow data).

The trainer 120 may train the prediction model 200 to predict the information (the number of imported cases, etc.) on the confirmed cases flowing into the destination country after the reference time point, from the input data before the reference time point. The prediction model 200 may be configured with a hierarchical prediction model so as to learn complex spatio-temporal relationships affecting the spread of infectious diseases. For example, the prediction model 200 may be configured to be composed of a risk prediction model per country that predicts the infectious disease information per country, being an infection risk over time, a risk prediction model per group that predicts the infection disease information (information on imported cases, such as the number of imported cases) per group to which countries belong, and a converged risk prediction model that predicts the number of imported cases from the infectious disease information per group through learning the correlation between groups.

For example, the trainer 120 may train the prediction model 200 through a hierarchical objective function L as in Equation 1 until a hierarchical loss of the prediction model is minimized. The hierarchical objective function L may be a loss function that minimizes a prediction error between a prediction of the risk prediction model per group and a ground truth of each group, and a prediction error between a prediction of the converged risk prediction model and a ground truth (the number of actual imported cases).

$$\mathcal{L} = \beta \| y_C(t+1:t+k) - \hat{y}_C(t+1:t+k) \|_2^2 + $$
$$(1-\beta) \| y(t+1:t+k) - \hat{y}(t+1:t+k) \|_2^2$$

Equation 1

In Equation 1, C is a group to which a country belongs, and for example, the group may be a continent grouped regionally. For example, C may be one of the continents classified for infectious disease management by the Korea Disease Control and Prevention Agency (KDCA), and C may be classified into C={China, Asia outside China, Europe, America, Africa, Oceania, and the like}. β is a hyperparameter for adjusting a weight of error of group unit. $y_C(t+1:t+k)$ is a ground truth representing the number of actual imported cases of a group for k days, and $\hat{y}_C(t+1:t+k)$ is the number of imported cases of the group fork days predicted by the prediction model 200. y(t+1:t+k) is a ground truth representing the number of total imported cases actually confirmed for k days, and ŷ(t+1:t+k) is the number of total imported cases for k days predicted by the prediction model 200.

The predictor 130 may include the prediction model 200 trained by the trainer 120 or may interwork with the prediction model 200 established externally. The predictor 130 receives real-time data generated from the infectious disease-related data collected up to the current time, and inputs the received real-time data to the trained prediction model 200. The predictor 130 outputs information on imported cases predicted by the prediction model 200 with respect to the real-time data. The predictor 130 may output the number of confirmed cases flowing into the destination country for the next k days and/or an inflow risk. The predictor 130 may predict the number of entrants to the destination country and the number of confirmed cases flowing into the destination country for the next k days, and may output the inflow risk based on the number of imported cases compared to that of the entrants.

The predictor 130 may obtain infectious disease information per country by inputting infectious disease-related data (epidemic statistics data and inflow data) of the country into the risk prediction model per country of the prediction model 200. The infectious disease information may represent a current infection risk of the country, a trend of infectious disease, a degree of exchange with the destination country, and the like. The infectious disease information may further include the expected number of entrants from the corresponding country to the destination country and the number of imported cases. Referring to Table 1, epidemic statistics data includes one or more of the number of daily confirmed cases, the number of deaths, an infection derivative index, and search keyword data related to the infectious disease.

The infection risk and the trend of infectious disease may be calculated from the epidemic statistics data, being time-series data. Additionally, the degree of exchange between the corresponding country and the destination country may be calculated from the inflow data. The predictor 130 may predict the number of imported cases according to the expected number of entrants per country, based on the infection risk, the trend of infectious disease, and the degree of exchange. Here, the expected number of entrants per country may be predicted based on flight schedules of airlines, the total number of passengers on board of an airplane, and the reported arrival and departure records. Further, the expected number of entrants per country may be obtained through adjusting a general expected number of entrants in consideration of an immigration policy of each country and an airline policy.

The predictor 130 may obtain infectious diseases information of each group to which countries belong, through the risk prediction model per group of the prediction model 200. N countries are classified into m groups having geographic and economical relationships. And, the infectious disease information of the countries belonging to the group may be corrected based on contagion risk impact between countries within a group and then integrated through a fully-connected layer of the corresponding group. In this way, the infected disease information per group is corrected through the contagion risk impact between countries within the group preset in the risk prediction model per group, thereby correcting the number of confirmed cases flowing into the destination country from the corresponding group.

The predictor 130 may acquire final information on imported cases through the converged risk prediction model of the prediction model 200. The final information on imported cases may be the total number of imported cases and/or the inflow risk. Here, infectious disease information per group is corrected based on the correlation between groups with respect to the destination country, and then integrated. As a result, the infectious disease information per country may be re-corrected by country unit, and the re-corrected information may be used for predicting the information on imported cases.

The predictor 130 may store data, respectively obtained from the risk prediction model per country, the risk prediction model per group, and the converged prediction model, on an interworking database. Real-time data derived from the predictor 130 or the stored data may be provided with being visualized through a separate data providing module (not shown). The data providing module may be included in the prediction apparatus 100 or may be connected via a network. Further, the data providing module may process the prediction data in various formats, and then provide the processed data.

The predictor 130 may visualize predicted data and provide the visualized predicted data. The predictor 130 may visualize each prediction data derived from a country-level encoder 10, a group-level encoder 20, and a converged risk prediction model 30 in various formats such as a map, a graph, and a table, and then provide the visualized prediction data. In addition, the infection risk or the number of imported cases of each country or each group may be represented with different colors, with being high-lighted, or with a specific icon.

Hereinafter, a prediction model will be described in detail with reference to FIG. 3 to FIG. 5.

Figure 3:
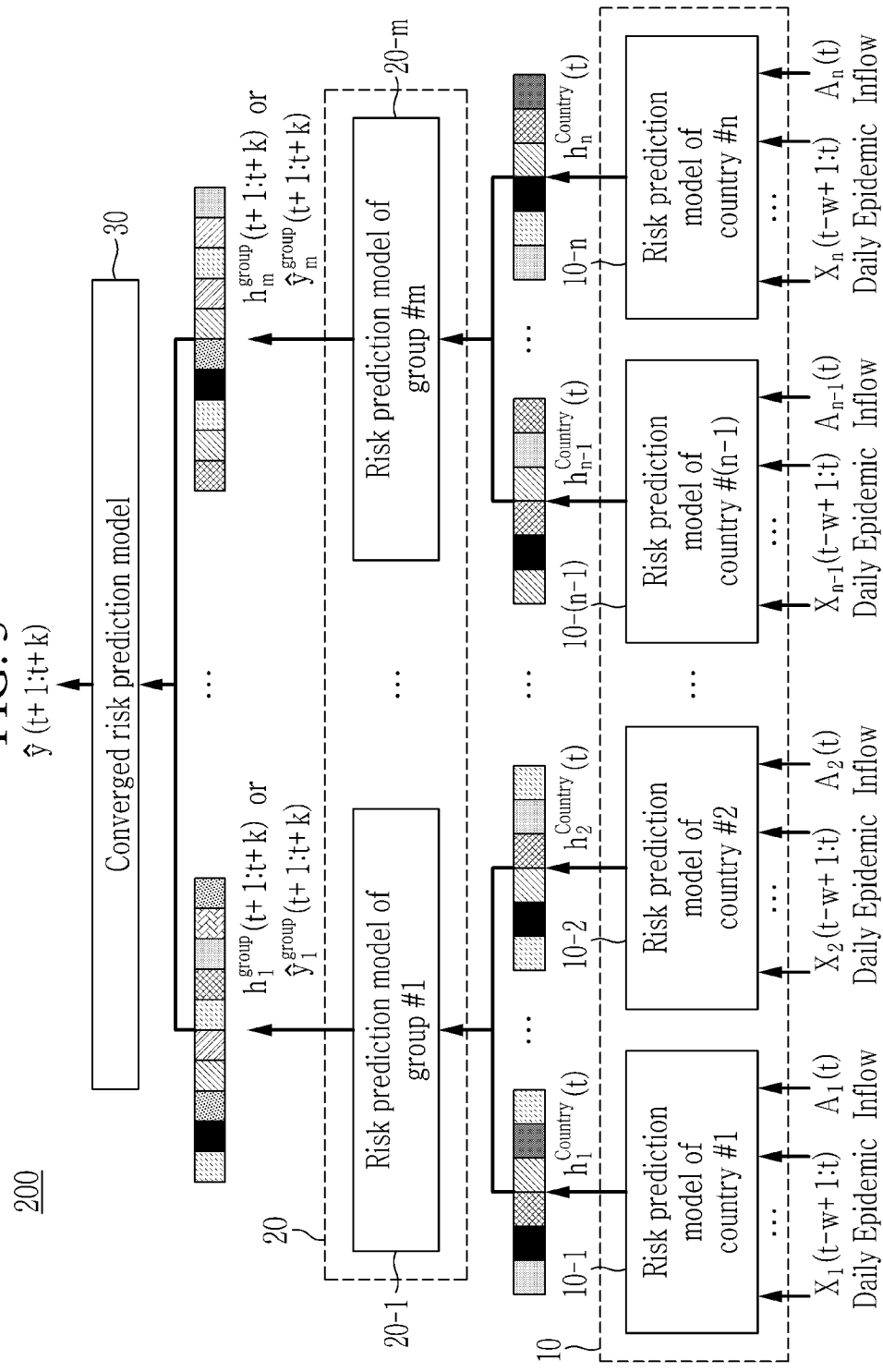
FIG. 3 is an example diagram showing a prediction model according to an embodiment.
Figure 4:
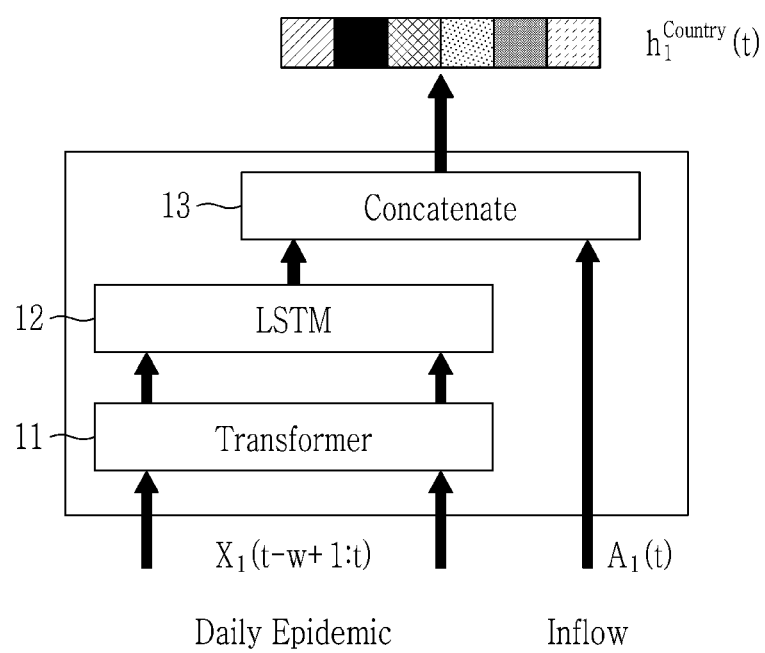
FIG. 4 is an example diagram showing a risk prediction model per country according to an embodiment.
Figure 5:
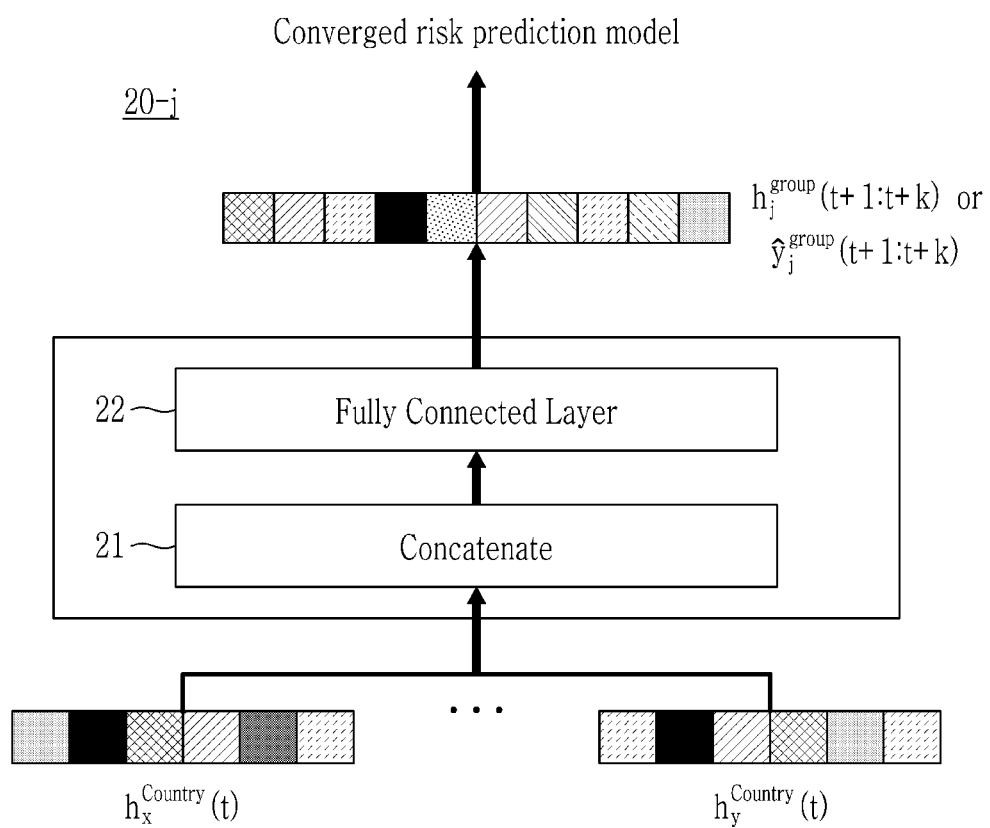
FIG. 5 is an example diagram showing a risk prediction model per group according to an embodiment.

FIG. 3 is an example diagram showing a prediction model according to an embodiment, FIG. 4 is an example diagram showing a risk prediction model per country according to an embodiment, and FIG. 5 is an example diagram showing a risk prediction model per group according to an embodiment.

Referring to FIG. 3, a prediction model 200 may include hierarchical networks composed of a country-level encoder 10, a group-level encoder 20, and a converged risk prediction model 30, which are closely connected in sequence. The prediction model 200 may include at least one group-level encoder 20. The hierarchical network structure of the prediction model 200 may be designed in various ways.

The country-level encoder 10 may be composed of risk prediction models of n countries 10-1, 10-2, . . . , and 10-n. The group-level encoder 20 may be composed of risk prediction models of m groups 20-1, . . . , and 20-m. Each risk prediction model is a sub-model of the prediction model 200, and may be named variously. A risk prediction model of the country-level encoder 10 and that of the group-level encoder 20 may have different network structures.

The risk prediction models of each country 10-1, 10-2, . . . , and 10-n receives infectious disease-related data of the corresponding country. The infectious disease-related data may include epidemic statistics data $X_i(t-w+1:t)$ of w days before from the current time t, and inflow data $A_i(t)$ between the corresponding country and a destination country. Here, w days may be set in consideration of an incubation period of an infectious disease. The epidemic statistics data may be daily epidemic data. The epidemic statistics data may include confirmed case-related data such as the number of confirmed cases per country, the number of deaths, search keywords data related to infectious disease per country, and the like. The inflow data may be international roaming service requested by a subscriber of a destination country to the corresponding country, traffic data such as flight data between the corresponding country and the destination country, arrival and departure status data, and the like.

The risk prediction models of each country 10-1, 10-2, . . . , and 10-n can output infectious disease information $h_i^{Country}(t)$ including an infection risk in the corresponding country. The infectious disease information may be expressed with latent variables indicating the infection risk, a trend of infectious disease, a degree of exchange, and the like. The infectious disease information may include the expected number of entrants from the corresponding country to the destination country and the number of imported cases in the future.

The risk prediction models of each country 10-1, 10-2, . . . , and 10-n can output the infectious disease information with being highlighted on a period having a singularity for the spread of the infectious disease in the corresponding country, based on the epidemic statistics data and the inflow data.

Here, the period having a singularity indicates a period during which a spread of infection is significantly increased by a specific event or a specific person, and may be set for a plurality of periods. For example, when a specific infected person was designated as a super-spreader and caused a multi-stage infection, the period during which the spread of infection is caused by the super-spreader may be set as the period having a singularity. Additionally, a period during which the spread of infection is significantly increased due to a specific event may be set as the period having a singularity.

The risk prediction models of each group 20-1, . . . , and 20-m receive infectious disease information output from the risk prediction models of countries belonging to the corresponding group. The risk prediction models of each group 20-1, . . . , and 20-m can correct and integrate the infectious disease information of countries to output the infectious disease information $h_j^{group}(t+1:t+k)$ of the corresponding group. The infectious disease information of a group may include an infection risk of a group and the information on imported cases. The information on imported cases predicted in group j can be explained as $\hat{y}_j^{group}(t+1:t+k)$. In this case, the risk prediction model of each group may output infectious disease information in which the infectious disease information of countries within the group is integrated.

Specifically, the information on imported cases may be the number of imported cases for the next k days. The information on imported cases may be the number of confirmed cases flowing from the group to the destination country. At this time, the risk prediction models of each group 20-1, . . . , and 20-m may correct the input infectious disease information of the countries with a contagion risk impact between countries within the group set according to the correlation between countries within the group. Then, the risk prediction models of each group 20-1, . . . , and 20-m can output information in which the corrected infectious disease information of countries is integrated.

The converged risk prediction model 30 receives prediction results output from all of the risk prediction models of groups 20-1, . . . , and 20-m. The converged risk prediction model 30 may receive the infectious disease information per group in the form of latent variables, or may receive the information on imported cases per group (the number of imported cases).

On the other hand, the converged risk prediction model 30 may learn a correlation between groups for the destination country while learning a relationship between the information on imported cases per group (e.g., the number of imported cases per group) and final information on imported cases in the destination country (e.g., the total number of imported cases). The correlation between groups may be set as a network parameter in learning process of predicting information on the total imported cases according to an infection risk/a trend of infectious disease by group. The converged risk prediction model 30 may correct the input information by applying a correlation for the confirmed cases of the infectious disease between groups, and then integrate the corrected information. As a result, the infectious disease information per country corrected in a group can be re-corrected at the group unit.

On the other hand, the converged risk prediction model 30 may receive geographic/economic relevance between groups (e.g., continent), and may establish a correlation between groups based thereon.

The converged risk prediction model 30 may be trained to predict the information $\hat{y}(t+1:t+k)$ on imported cases to the destination country for the upcoming k days, from the infectious disease information per group and to output the predicted information. The information on imported cases may be the total number of imported cases expected in the destination country for the upcoming k days. In a fully connected layer of the converged risk prediction model 30, the infectious disease information per group may be corrected and integrated.

In addition, the converged risk prediction model 30 may be trained to predict the number of entrants and imported cases into the destination country and to output an inflow risk, being a ratio of the imported cases to the entrants.

As such, the prediction model 200 does not predict the information on imported cases to the destination country by using the infectious disease information of each country as it is, but predicts the information on imported cases while correcting the infectious disease information per country within a group through a hierarchical network structure and re-correcting the corrected information by group. Thus, a prediction reflecting a complex spatio-temporal relationship affecting the spread of infectious disease may be performed.

Since the prediction model 200 allocates an independent risk prediction model for each country, it is possible to configure a network structure for a destination country by adding or deleting a target country from which the infectious disease information is extracted according to the destination country. Settings for analysis country may be set and changed by an administrator based on infectious disease situation. In addition, the prediction model 200 can freely set a relationship between countries and a group based on the infectious disease situation. For example, a country-group relationship where China having a singularity and remaining Asian countries are connected into different groups in an early stage of COVID-19 may be changed to a network structure connecting China as an Asian group.

Actually, since the infectious disease information derived for each country is generated from the infectious disease situation of a country, the infectious disease situations of neighboring countries are not reflected. However, since frequent exchanges are made between geographically adjacent countries or economically close countries, these countries may mutually have an influence on the spread of infectious diseases. For example, when a risk in a certain country is high due to an explosion in the number of confirmed cases, it is highly likely that the infectious disease will spread in the near future in the neighboring other countries, even though the current risk is low. Meanwhile, the influences between countries may differ depending on the continents. For example, since exchanges between countries in Europe where transportation is developed and the concept of borders is relatively weak are thrived compared to Africa where transportation infrastructure is relatively less expanded, degrees of infection risks between neighboring countries in Europe may greatly affect each other. In order to reflect the geographic/economic relevance, the prediction model 200 can correct the infectious disease information per country by multiplying the infectious disease information per country with the infection risk per country set as a learnable parameter after classifying countries into groups (e.g., continents). The infectious disease information of countries corrected in this way is concatenated in the fully-connected layer and then is output as a prediction result of the corresponding group.

Also, the degree of exchange between the destination country and each group may be different. For example, Korea, being the destination country, has very close relationships with countries on the Asian continent, which enables many personal and material exchanges. Oppositely, Korea may not have active exchanges with countries on the African continent. In fact, it will be highly likely that confirmed cases flow into Korea from countries on the Asian continent, and it will be less likely that the confirmed cases flow into Korea from countries on the African continent. Therefore, when predicting the information on imported cases from each group to the destination country, the prediction model 200 corrects the infectious disease information of countries belonging to each group by reflecting the correlation between the groups for the destination country. The prediction model 200 may re-correct the infectious disease information per country by multiplying the infectious disease information with the correlation between groups set as the learnable parameter (weight).

Like this, it can be seen that considering the infectious disease information changing over time within a country and exchange relationship between countries is required for predicting the information on confirmed cases that will flow into a specific country. When the imported cases are predicted in the way that the infectious disease information per country is enumerated and then simply gathered, it is difficult for the prediction model to learn complex contexts in the learning process. On the other hand, since the prediction model 200 of the present disclosure has a network structure hierarchically divided into a prediction per country, a prediction per group, and final prediction, a hierarchical loss can be learned, thereby increasing prediction ability.

Referring to FIG. 4, a sub-prediction model 10-$i$ of an i-th ($i=1\sim n$) country may consist of a transformer layer 11, a long short-term memory (LSTM) layer 12 and a concatenate layer 13. A risk prediction model 10-$i$ of the i-th country may receive an input of epidemic statistics data $X_i(t-w+1:t)$ collected during a certain period in the i-th country, and inflow data $A_i(t)$ between the i-th county and the destination country. The epidemic statistics data may include the number of confirmed cases, the number of deaths, search keywords, and the like that are collected in the i-th country from $(t-w+1)$ day to t day, and w may be set in consideration of an incubation period of the infectious disease. Here, the LSTM layer 12 is a network that processes time-series data and is a type of recurrent neural network (RNN). An output from a last cell summarizing an entire sequence is stored in the LSTM. Here, the LSTM layer 12 may be replaced with another type of network that processes time-series data.

The epidemic statistics data, being time-series data, can be expressed as a characteristic such as an infection risk, via the transformer layer 11 and the LSTM layer 12. The transformer layer 11 can highlight a period of high infection risk in the epidemic statistics data $X_i(t-w+1:t)$, and can output $h_i^{TM}(t-w+1:t)$. Here, the period of high infection risk may have the same meaning as the period having a singularity described above. The transformer layer 11 can highlight a period in which cases having had a great impact on the spread of the infectious disease occurred, through an attention technique.

The LSTM layer 12 receives an output from the transformer layer 11 and outputs a temporal trend of the infectious disease. The LSTM layer 12 may receive epidemic statistics data in which the period having a singularity is highlighted by the transformer layer 11. $h_i^{LSTM}(t)$ output from the LSTM layer 12 may represent the infection risk of the i-th country, the trend of infectious diseases, and the like at the time point of t.

The concatenate layer 13 integrates the output of the LSTM layer 12 and the inflow data $A_i(t)$. The concatenate layer 13 can infer a degree of exchange between the i-th country and the destination country from the inflow data $A_i(t)$, and integrate the inferred degree of exchange with the output of the LSTM layer 12.

The concatenate layer 13 may output the infectious disease information $h_i^{Country}(t)$ of the i-th country. The infectious disease information $h_i^{Country}(t)$ may be a latent representation indicating a risk of the infectious disease of the i-th country to the destination country at the time point of t. In addition, the infectious disease information may represent the trend of the infectious disease, the degree of exchange with the destination country, and the like. In addition, the infectious disease information may include the expected number of entrants from the i-th country to the destination country, the number of imported cases, and the like.

Referring to FIG. 5, a risk prediction model 20-j of a j-th (j=1~m) group may be composed of a concatenate layer 21 and a fully connected layer 22. The concatenate layer 21 receives an input of infectious disease information per country.

The concatenate layer 21 and the fully connected layer 22 receive the input of the infectious disease information per country, and output infectious disease information $h_j^{group}(t+1:t+k)$ predicted in a corresponding group. The infectious disease information predicted in the corresponding group may be expressed as in Equation 2.

$$h_j^{group}(t+1:t+k) = \varnothing(\text{concat}([\ldots, h_i^{Country}(t), \ldots]); \Theta_j^\Phi)$$

Equation 2

In equation 2, ø is a fully-connected network with one hidden layer for the j-th group and is parameterized by $\Theta_j^\Phi$ with the ReLU activation function.

The infectious disease information may be a series of latent variables inferred from the group, and specifically may be information on confirmed cases flowing into a destination country from the group for an upcoming certain period. The information the imported cases can be expressed as the number of imported cases $\hat{y}_j^{group}(t+1:t+k)$ for the next k days. On the other hand, the concatenate layer 21 and the fully connected layer 22, which have learned a correlation between countries within a group geographically/economically related during a training process, can set a contagion risk impact between countries as a weight according to the correlation between countries within the group, can correct the input infectious disease information per country using the weight, and then can predict the information on imported cases.

The result output from the fully connected layer 22 of each group is input to a converged risk prediction model 30 and then used to predict the total number of imported cases flowing into the destination country for the next k days.

Figure 6:
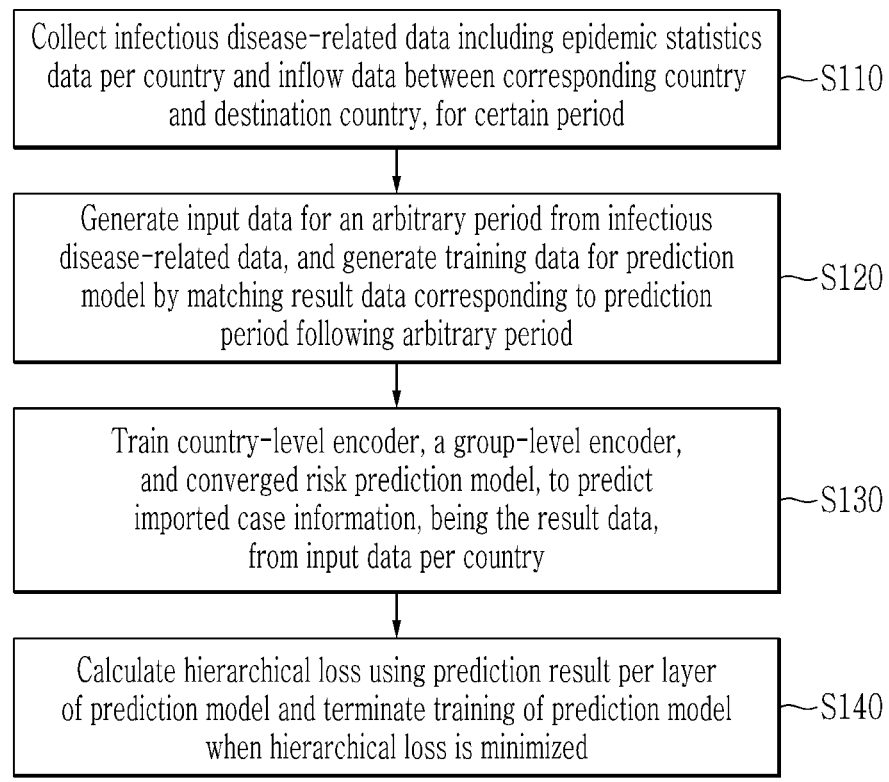
FIG. 6 is a flowchart showing a method for training a prediction model according to an embodiment.

FIG. 6 is a flowchart showing a method for training a prediction model according to an embodiment.

Referring to FIG. 6, a prediction apparatus 100 collects infectious disease-related data including epidemic statistics data per country and inflow data between a corresponding country and a destination country, for a certain period (S110).

The prediction apparatus 100 generates input data for an arbitrary period from the infectious disease-related data, and generates training data for a prediction model by matching result data corresponding to a prediction period following the arbitrary period (S120). The input data are epidemic statistics data per country and inflow data for a certain period defined as in Table 1, and the result data may be the number of actual imported cases identified in the destination country during a prediction period defined as in Table 2. The prediction apparatus 100 can match input data per country for a certain period (monitoring period) before a reference time point t in the infectious disease-related data and the number of actual imported cases identified in the destination country for a certain period after the reference time point t, as the result data. The prediction apparatus 100 may pre-process the input data and the result data to fit for an input format and a task of the prediction model.

The prediction apparatus 100 trains a hierarchical prediction model 200, being composed of a country-level encoder 10, a group-level encoder 20, and a converged risk prediction model 30, to predict information on imported cases, being the result data, from the input data per country (S130). The country-level encoder 10 may be composed of risk prediction models per country 10-1, 10-2, ..., and 10-n, and each risk prediction model may learn a task for extracting the infectious disease information per country from the input data. The group-level encoder 20 may be composed of risk prediction models per group 20-1, ..., and 20-m, and each risk prediction model may learn a task for extracting the infectious disease information per group from the infectious disease information of countries belonging to a group. The converged risk prediction model 30 may learn a task for predicting the total number of imported cases from the infectious disease information per group. The risk prediction model per country in the country-level encoder 10 may extract the infectious disease information including an infection risk from the epidemic statistics data and inflow data of each country. The risk prediction model per group of the group-level encoder 20 may extract the infectious disease information (e.g., the number of imported cases) of the group by correcting and integrating the infectious disease information per country.

The prediction apparatus 100 calculates a hierarchical loss using a prediction result per layer of the prediction model 200, and terminates training of the prediction model 200 when the hierarchical loss is minimized (S140). For example, the hierarchical loss can be defined as a sum of a prediction error for the number of actual imported cases of each group and a prediction error for the total number of actual imported cases, as shown in Equation 1. When the hierarchical loss is minimized, training of the prediction model 200 may be terminated. As described above, the prediction model 200 has a network structure hierarchically divided into a prediction per country, a prediction per group, and a final prediction. Therefore, the hierarchical loss can be learned, which improves prediction ability. Namely, through learning of the hierarchical loss, an accuracy of the risk prediction model can be improved by and large while improving accuracies at levels of the risk prediction model per country and the risk prediction model per group.

Referring to Table 3, the prediction model derives the prediction results in the order of a country-level encoder, a continent-level encoder, and a prediction layer, and repeats training so as to minimize the hierarchical loss defined as in Equation 1. The prediction model may calculate the hierarchical loss, and repeat training while updating parameters for an entire network through backpropagation.

TABLE 3

| Algorithm 1 Hi-COVIDNet Training |
| --- |
| INPUT: $X_i(t)$, $A_i(t)$, and $y(t)$ (see §3.1); k days to predict |
| OUTPUT: Set of the optimal model parameters $\Theta_s$ |
| 1: $\Theta^{TM}, \Theta^{LSTM}, \Theta^\Phi, \Theta^\Psi \leftarrow$ Initialize model, parameters; |
| 2: for epoch = 1 to epoch do |
| 3:   for each t ∈ { training days } /* Mini-batch */ |
| 4:     /* COUNTRY-LEVEL ENCODER */ |
| 5:     for each i ∈ { countries } do |
| 6:       Compute $h_i^{TM}(t)$ |
| 7:       Compute $h_i^{LSTM}(t)$ |
| 8:       Compute $h_i^{Country}(t)$ |
| 9:     /* CONTINENT-LEVEL ENCODER */ |
| 10:    for each j ∈ { continents } do |

TABLE 3-continued

Algorithm 1 Hi-COVIDNet Training

11:   Compute $h_j^{Coontinent}$ (t+1:t+k)
12:   /* PREDICTION LAYER */
13:   Estimate ŷ(t+1:t+k)
14:   /* MODEL UPDATE */
15:   Compute the loss L
16:   Θ* ← Θ* − αVL;
17: return Θ*;

Meanwhile, the prediction apparatus 100 can retrain the prediction model based on the infectious disease-related data at a certain cycle or an arbitrary time point.

In a learning process, the prediction model 200 can infer the infection risk per country, a trend of infectious diseases, and a degree of exchange from the infectious disease-related data including epidemic statistics data and inflow data, and can predict the number of imported cases based on the expected number of entrants per country. At this time, the prediction model 200 may learn the contagion risk impact between countries within a group during the learning process, and correct the infectious disease information per country with the contagion risk impact. In the learning process of the risk prediction model per group of the prediction model 200, a correlation between countries may be analyzed based on the infection risks and the trends of infectious diseases in the countries within the group, and the contagion risk impact may be set as a weight. For example, it is assumed that country A and country B has similar trends of infectious diseases while country C has different characteristics from other countries, among country A, country B, and country C grouped as a same continent. In this case, since a correlation between country A and country B is high, the contagion risk impact between country A and country B may set highly in the risk prediction model per group. Meanwhile, country C may be set to have a low contagion risk impact on other countries having low correlations. This contagion risk impact may be derived from iterative learning process of the risk prediction model per group.

The risk prediction model per group can output the corrected infection risk and the corrected number of imported cases per country with being integrated per group, or can output as separate data for each country in a group. In the learning process of the converged risk prediction model of the prediction model 200, a group-wise correlation for the destination country is analyzed, and parameters according to an inter-group correlation may be set as weights. For example, information on inflowing infectious diseases may be corrected group-wise according to a correlation for the infection risk and the trend of infectious diseases between a first group (Country A, Country B, and Country C) and a second group (Country D, Country E). At this time, a re-corrected value based on the correlation between the groups may be equally applied to countries within the group. For example, in a situation that the first group and the second group have a certain geographic relevance or economic relevance equal to or greater than a certain value and the number of confirmed cases or the trend of confirmation has a positive correlation, the infection risk or the trend of infectious disease of the second group may be increased by the infection risk or the trend of infectious disease of the first group. Here, the correlation for the confirmed cases per group, such as geographic or economic relevance, whether there is a correlation, a degree of correlation, and whether a weight is applied between groups, is a parameter automatically derived through learning. Namely, a weight for an input may be applied in the converged prediction model so that the number of actual imported cases can be predicted from the input infectious disease information per group (including infectious disease information per country).

Figure 7:
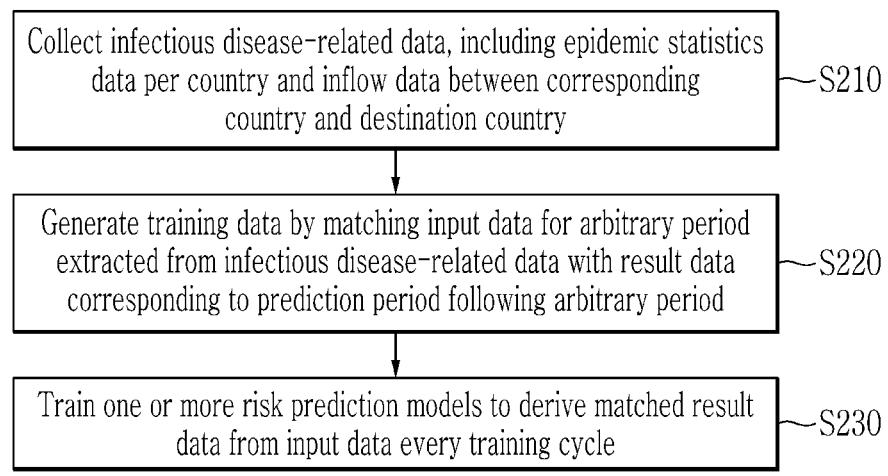
FIG. 7 is a flowchart showing a method for training a prediction model according to another embodiment.

FIG. 7 is a flowchart showing a method for training a prediction model according to another embodiment.

Referring to FIG. 7, the prediction apparatus 100 collects infectious disease-related data, including epidemic statistics data per country and inflow data between a corresponding country and a destination country (S210).

The prediction apparatus 100 generates training data by matching input data for an arbitrary period extracted from the infectious disease-related data with result data corresponding to a prediction period following the arbitrary period (S220).

The prediction apparatus 100 trains one or more risk prediction models to derive matched result data from the input data every training cycle (S230). The prediction apparatus 100 may train to predict the number of imported cases based on the expected number of entrants per country by respectively deriving the infection risk per country, the trend of infectious disease, and a degree of exchange from the input data, and to derive the result data as the number of imported cases that is corrected based on a correlation between contagion risk impact among countries grouped based on geographic or economical relevance and confirmed cases of infectious diseases by group unit.

The risk prediction model trained by the prediction apparatus 100 may include a risk prediction model per country that predicts infectious disease information including the number of confirmed cases flowing into each country based on the infection risk by country unit and a degree of exchange between the corresponding country and the destination country, a risk prediction model per group that corrects the number of imported cases of each country according to the contagion risk impact of countries grouped based on the geographic or economic relevance, and a converged risk prediction model that predicts the total number of imported cases flowing into the destination country through re-correcting the infectious disease information per country by applying a correlation for confirmed cases of the infectious disease of group unit to the corrected infectious disease information per country. The prediction apparatus 100 may successively train the risk prediction model per country, the risk prediction model per country, and the converged risk prediction model, and then may calculate a hierarchical loss based on the results for the number of imported cases predicted or corrected by each model. Further, prediction apparatus 100 may update parameters of the risk prediction model per country, the risk prediction model per group, and the converged risk prediction model by way of error backpropagation so that the calculated hierarchical loss is minimized.

Figure 8:
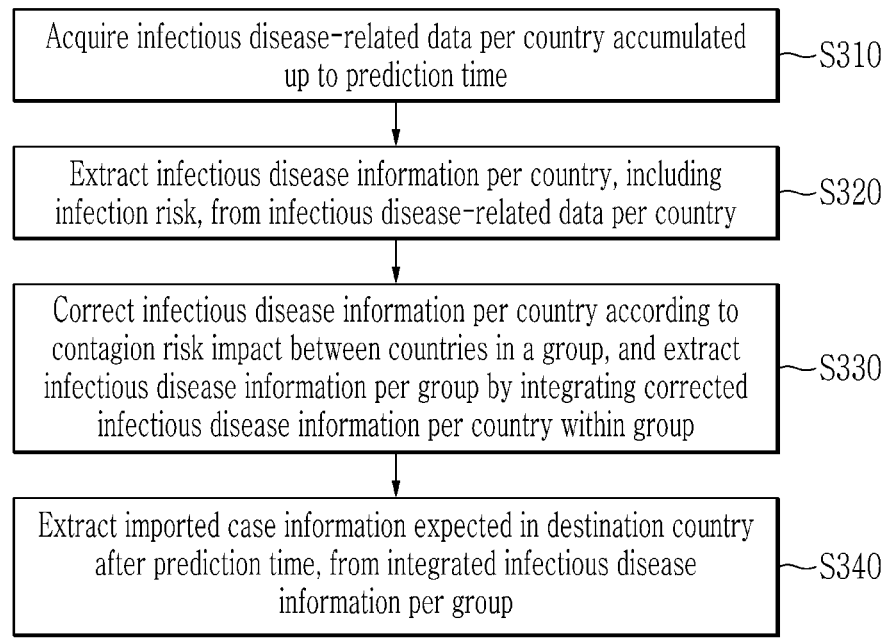
FIG. 8 is a flowchart showing a method for predicting imported cases according to an embodiment.

FIG. 8 is a flowchart showing a method for predicting imported cases according to an embodiment.

Referring to FIG. 8, a prediction apparatus 100 acquires infectious disease-related data per country accumulated up to prediction time (S310). The infectious disease-related data may include epidemic statistics data and inflow data.

The prediction apparatus 100 extracts the infectious disease information per country including an infection risk from the infectious disease-related data per country (S320). The prediction apparatus 100 may extract the infectious disease information after highlighting a period with a high infection risk in the epidemic statistics data.

The prediction apparatus 100 corrects the infectious disease information per country according to a contagion risk impact between countries in a group, and extracts infectious disease information per group by integrating the corrected infectious disease information per country in the group (S330). The countries may be classified into groups based on geographic/economic relevance. For example, the prediction apparatus 100 may set, as a group, a continent (East Asia, Oceania, America, and the like) in which countries are located. During learning process of the prediction model 200, the contagion risk impact between countries within the group is set as a weight of the prediction model 200.

The prediction apparatus 100 extracts information on imported cases expected in a destination country after the prediction time, from the integrated infectious disease information per group (S340). The prediction apparatus 100 may predict the information of imported cases by using the infectious disease information per group corrected based on a correlation between the destination country and the groups. The imported case information may be the number of imported cases predicted for the upcoming k days.

Figure 9:
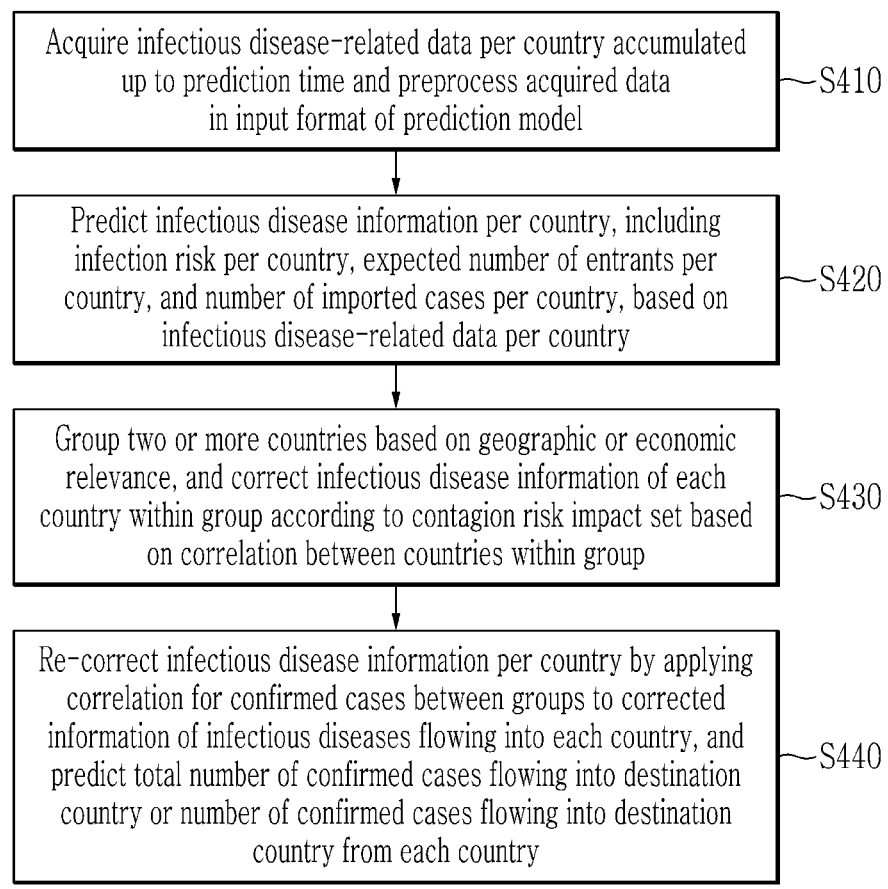
FIG. 9 is a flowchart showing a method for predicting imported cases according to another embodiment.

FIG. 9 is a flowchart showing a method for predicting imported cases according to another embodiment.

Referring to FIG. 9, a prediction apparatus 100 acquires infectious disease-related data per country accumulated up to the prediction time and preprocesses the acquired data in an input format of a prediction model 200 (S410). The infectious disease-related data may include epidemic statistics data and inflow data. The prediction apparatus 100 may classify by country the epidemic statistics data per country and the inflow data, and preprocess the data as an input format of a trained risk prediction model per country.

The prediction apparatus 100 predicts the infectious disease information per country, including an infection risk per country, the expected number of entrants per country, and the number of imported cases per country, based on the infectious disease-related data per country (S420). The prediction apparatus 100 may derive the infection risk and a trend of infectious disease by highlighting a period (singularity period) with a high infection risk in the epidemic statistics data. And the prediction apparatus 100 may infer a degree of exchange between each country and a destination country from the inflow data. The prediction apparatus 100 may predict the expected number of entrants per country into the destination country, the number of imported cases per country, and the like, based on infectious disease information per country including the infection risk, the trend of infectious disease, a degree of exchange, and the like.

Prediction apparatus 100 groups two or more countries based on geographic or economic relevance, and corrects the infectious disease information of each country within the group according to a contagion risk impact set based on a correlation between countries within the group (S430). The countries may be classified into groups based on geographic/economic relevance. For example, the prediction apparatus 100 may set, as a group, a continent (East Asia, Oceania, America, and the like) in which countries are located. The contagion risk impact between countries within the group is automatically derived during learning process of the prediction model 200, according to the correlation between countries based on the infection risk of countries within the group, and is set as the weight of the prediction model 200.

The prediction apparatus 100 re-corrects the infectious disease information per country by applying the correlation for the confirmed cases between groups to the corrected information of infectious diseases flowing into each country, and then predicts the total number of confirmed cases flowing into the destination country or the number of confirmed cases flowing into the destination country from each country (S440). In the process of correcting the infectious disease information per group according the correlation between groups, the infectious disease information per country is re-corrected. The prediction apparatus 100 can input the corrected infectious disease information per country to the trained converged risk prediction model. The prediction apparatus can re-correct the information on infectious disease flowing into each country, by country unit, according to the correlation between groups that is automatically derived based on the infection risk of group unit and the trend of infectious disease of group unit during learning process of the converged risk prediction model. Then, the prediction apparatus 100 can predict the number of imported cases flowing into each country, the number of imported cases per group, and the total number of imported cases through the re-corrected infectious disease information per country.

After the prediction model 200 predicted the total number of entrants from the extracted infectious disease information per country, the inflow risk that is a ratio of imported cases to the entrants can be output.

The prediction apparatus 100 may process data or information extracted during predicting the total number of confirmed cases as visualized data and then provide the visualized data. The data or information extracted during predicting the total number of confirmed cases may include the total number of imported cases, the infection risk per country, the trend of infectious disease per country, initially extracted infectious diseases information per country, corrected infectious diseases information per country, and re-corrected infectious diseases information per country, and the like.

Figure 10:
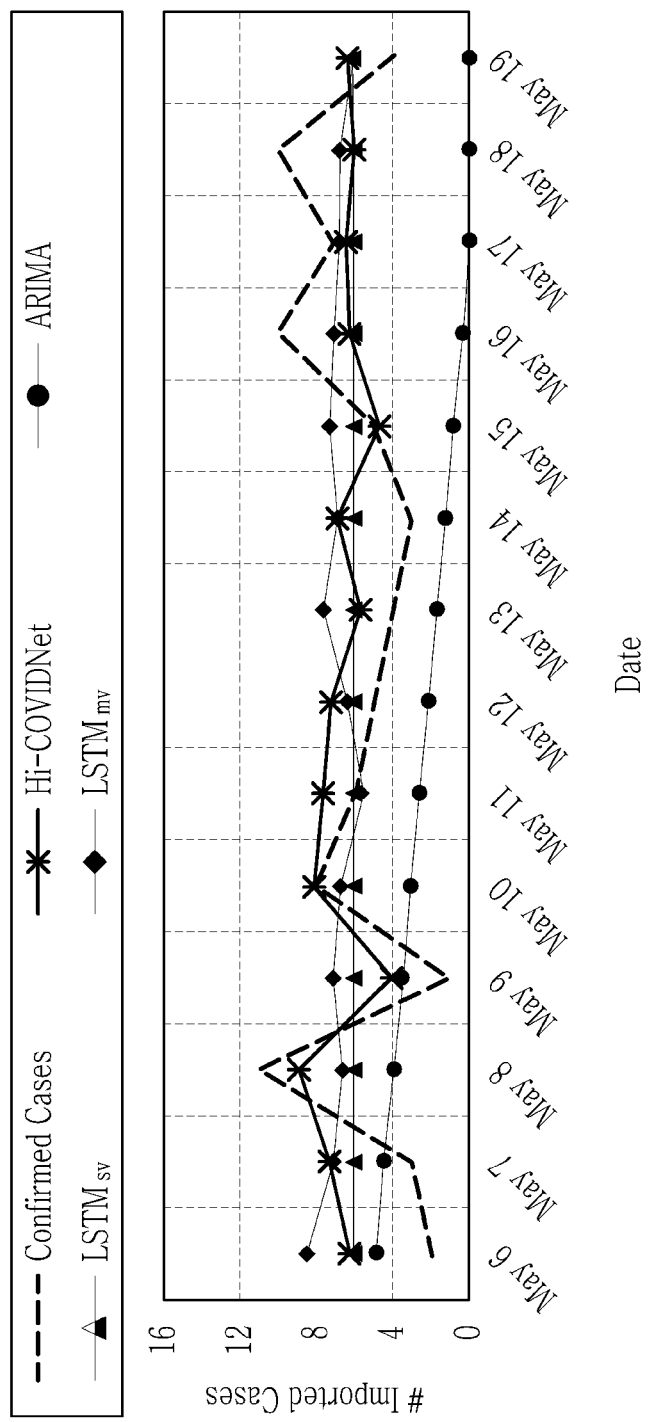
FIG. 10 is a graph showing a result of evaluating performance of a prediction model according to an embodiment.

FIG. 10 is a graph showing a result of evaluating performance of a prediction model according to an embodiment.

Referring to FIG. 10, an autoregression integrated moving average model (ARIMA) and a long-short term memory (LSTM), being previously known time-series prediction algorithms, are used in order to evaluate performance of a prediction model 200 named as Hi-COVIDNet. Here, the ARIMA defines a relationship between the present and a trend, and gets to use only a variable of the collected number of imported cases. LSTM_sv uses only a single variable, and LSTM_mv uses multiple variables.

In order to evaluate a prediction method of the present disclosure and to explain a difference from previously known methods, training data and test data for a certain period are used. Here, if the training data is data from March 22 to May 5, the test data represent from May 6 to May 19. And a window size w is set to 14 in response to an incubation period of an infectious disease (e.g., COVID-19). A root mean square error (RMSE) defined as in the following Equation 3 may be used as a prediction error.

$$RMSE = \sqrt{\frac{1}{k}\sum_{i=1}^{k}(y_i(t+1:t+k) - \hat{y}_i(t+1:t+k))^2}$$ Equation 3

In Equation 3, y represents the number of actual imported cases for next k days from day t, and $\hat{y}$ represents the number of predicted imported cases for the next k days from day t.

First, through examining the numbers of imported cases predicted by a proposed method (Hi-COVIDNet), ARIMA, LSTM_sv, and LSTM_mv as shown in FIG. 10, it can be seen that the number of imported cases predicted by the proposed method (Hi-COVIDNet) is the closest to the number of actual imported cases.

Next, as shown in Table 4, through examining prediction errors for prediction periods of 7 days and 14 days calculated by the proposed method (Hi-COVIDNet), ARIMA, LSTM_sv, and LSTM_mv, it can be seen that the proposed method (Hi-COVIDNet) has the lowest prediction error compared to other prediction models regardless of the prediction periods.

TABLE 4

| Prediction model | MAY 6~12(k = 7) | MAY 6~12(k = 14) |
|---|---|---|
| ARIMA | 0.4931 | 0.6243 |
| $LSTM_{mv}$ | 0.4600 | 0.4274 |
| $LSTM_{sv}$ | 0.5188 | 0.4621 |
| Hi-COVIDNet | 0.4373 | 0.4045 |

As such, the prediction model 200 can more precisely predict the number of imported cases by using hierarchically extracted multiple variables.

Meanwhile, the performances evaluated by varying a hierarchical structure, a transformer, and input data in the proposed method (Hi-COVIDNet) are as shown in Table 5.

TABLE 5

| Hi-COVIDNet variant | RMSE |
|---|---|
| w/o inter-country data | 0.6086 |
| w/o continent-level encoder | 0.5800 |
| w/o Transformer | 0.4543 |
| Hi-COVIDNet | 0.4045 |

Here, w/o inter-country data represents not using inter-country data as input data, and specifically indicates a model to which roaming and flight data set is not input. A w/o continent-level encoder excludes a risk prediction model per group and is a prediction model that does not consider contagion risk impact between countries within a group. A w/o transformer is a prediction model that does not include a transformer layer highlighting a period with a singularity in a risk prediction model per country.

Referring to Table 5, it can be seen that using inflow data improves prediction accuracy when the prediction model 200 extracts infectious disease information per country. In addition, it can be seen that the prediction accuracy is improved by correcting the infectious disease information per country according to the contagion risk impact between countries within the group in the risk prediction model per group.

Figure 11:
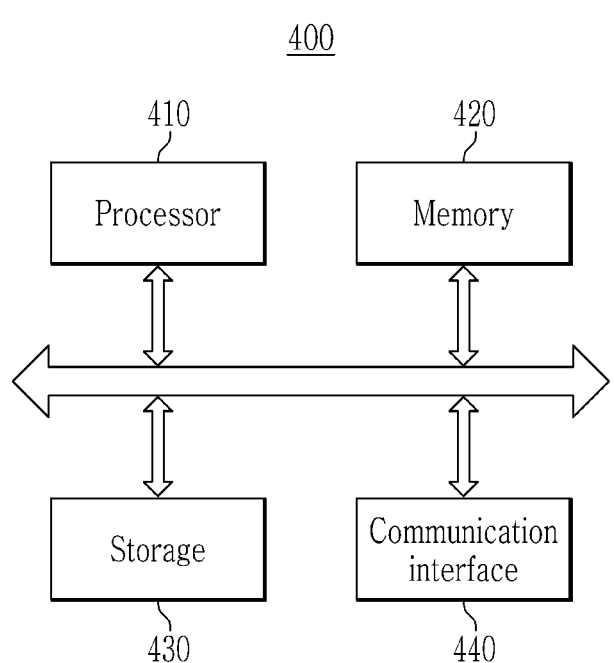
FIG. 11 is a hardware configuration diagram of a computing device according to an embodiment.

FIG. 11 is a hardware configuration diagram of a computing device according to an embodiment.

Referring to FIG. 11, a prediction apparatus 100 or components of the prediction apparatus 100 such as a preprocessor 110, a trainer 120, and a predictor 130 may be implemented as a computing device 300 operated by at least one processor.

Hardware of a computing device 400 may include at least one processor 410, a memory 420, a storage 430, and a communication interface 440, which may be connected via a bus. Additionally, various components such as an input device and an output device may be further included.

The processor 410 is a device that controls an operation of the computing device 400, and may be a processor of various types that processes instructions included in a computer program. For example, the processor 410 may be configured to include at least one of a central processing unit (CPU), a micro processor unit (MPU), a micro controller unit (MCU), a graphic processing unit (GPU), or any type of processor well known in the art of the present disclosure.

The memory 420 loads a corresponding computer program so that instructions described to execute the operation of the present disclosure are processed by the processor 410. The memory 420 may be, for example, a read only memory (ROM), a random access memory (RAM), and the like.

The storage 430 stores various data, computer programs, and the like required to execute the operation of the present disclosure. The communication interface 440 may be a wired/wireless communication module.

The computer program includes instructions executed by the processor 410 and is stored on a non-transitory computer readable storage medium. The instructions make the processor execute the operation of the present disclosure. The computer program may be downloaded via a network or sold as a product. Accordingly, the prediction model may be implemented as a computer program executed by the processor 410.

As described above, according to an embodiment, confirmed cases flowing from abroad can be precisely estimated by considering external factors, such as a degree of exchange between a corresponding country and a destination country and a contagion risk impact between neighboring countries, in addition to epidemic statistics data. Further, domestic spread may be prevented through preemptive reinforcement of immigration inspection based on the predicted number of imported cases.

According to the present disclosure, by predicting the number of confirmed cases from abroad, a quarantine policy can be established and resources can be allocated in advance. As a result, national risk caused by infectious diseases flowing from abroad can be minimized Although an embodiment of the present invention has been described in detail above, the scope of the present invention is not limited thereto, and a person of an ordinary skill in using the basic concept of the present invention defined in the following claims range Various modifications and improvements of the art also belong to the scope of the present invention.

What is claimed is:

1. A method for operating an apparatus for predicting confirmed cases of an infectious disease, the method comprising:

generating training data by matching input data for an arbitrary period with result data corresponding to a prediction period following the arbitrary period, from collected epidemic statistics data per country and inflow data between a corresponding country and a destination country; and training one or more risk prediction models to derive matched result data from the input data at each training cycle, wherein the training the risk prediction model comprises hierarchically training under a process to:

predicting number of imported cases based on expected number of entrants per country through respectively deriving an infection risk per country, a trend of infectious disease, a degree of exchange from the input data;

grouping two or more countries based on geographic or economic relevance;

correcting the number of imported cases based on correlation for confirmed cases of the infectious disease between groups and a contagion risk impact set according to a correlation between grouped countries; and outputting the corrected number of imported cases, as the result data.

2. The method of claim 1, wherein the risk prediction model comprises
- a risk prediction model per country that predicts infectious disease information, including the number of confirmed cases flowing into each country, based on the infection risk by country unit and a degree of exchange between a corresponding country and a destination country,
- a risk prediction model per group that corrects the number of imported cases per country according to the contagion risk impact of countries grouped based on geographic or economic relevance, and
- a converged risk prediction model that predicts total number of imported cases to the destination country by re-correcting the infectious disease information per country, by applying a correlation for confirmed cases between groups to the corrected infectious disease information per country by group unit.

3. The method of claim 2, wherein the risk prediction model per country
- derives the infection risk and the trend of infectious disease at a current time by highlighting a period with a singularity on a spread of the infectious disease in epidemic statistics data per country, wherein the epidemic statistics data per country includes one or more of number of daily confirmed cases, number of deaths, an infection derivative index, and search keywords data related to infectious diseases,
- estimates a degree of exchange with the destination country per country based on inflow data, wherein the inflow data includes one or more of number of customers having subscribed to a roaming service per country, arrival and departure status data per country, number of airlines entering into a country, and flight records of the airlines, and
- predicts expected number of entrants per country and the number of imported cases per country, based on the infection risk, the trend of infectious disease, and the degree of exchange.

4. The method of claim 3, wherein the contagion risk impact is automatically derived according to a correlation between countries based on the infection risk and the trend of infectious disease of countries within each group, during learning process of the risk prediction model per group, and
- wherein the correlation for confirmed cases between groups is automatically derived based on the infection risk by group unit and the trend of infectious disease of group unit, during learning of the converged risk prediction model.

5. The method of claim 4, wherein the training the risk prediction model comprises
- after successively training the risk prediction model per country, the risk prediction model per group, and the converged risk prediction model, calculating a hierarchical loss based on a result of number of imported cases predicted or corrected by each model, and
- updating parameters of the risk prediction model per country, the risk prediction model per group, and the converged risk prediction model, based on a loss of each layer, through error backpropagation so that the calculated hierarchical loss is minimized.

* * * * *